United States Patent
Schoepgens et al.

(10) Patent No.: US 11,154,478 B2
(45) Date of Patent: Oct. 26, 2021

(54) SELF-HEATING AGENTS FOR REDUCTIVE DECOLORIZATION OF DYED KERATINOUS FIBERS

(71) Applicant: Henkel AG & Co. KGaA, Duesseldorf (DE)

(72) Inventors: Juergen Schoepgens, Schwalmtal (DE); Torsten Lechner, Langenfeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 617 days.

(21) Appl. No.: 15/920,844

(22) Filed: Mar. 14, 2018

(65) Prior Publication Data

US 2018/0263880 A1  Sep. 20, 2018

(30) Foreign Application Priority Data

Mar. 15, 2017  (DE) .......................... 102017204282.6

(51) Int. Cl.
| | | |
|---|---|---|
| *A61Q 5/08* | (2006.01) | |
| *A61K 8/46* | (2006.01) | |
| *A61K 8/22* | (2006.01) | |
| *A61K 8/41* | (2006.01) | |

(52) U.S. Cl.
CPC ................. *A61K 8/46* (2013.01); *A61K 8/22* (2013.01); *A61K 8/41* (2013.01); *A61Q 5/08* (2013.01); *A61K 2800/882* (2013.01)

(58) Field of Classification Search
None
See application file for complete search history.

(56) References Cited

U.S. PATENT DOCUMENTS

| 2012/0315236 A1* | 12/2012 | Goutsis ................... A61K 8/22 |
| | | 424/62 |
| 2014/0190508 A1 | 7/2014 | Hawkes et al. |
| 2017/0128342 A1* | 5/2017 | Schoepgens ............. A61K 8/86 |

FOREIGN PATENT DOCUMENTS

| EP | 1300136 A2 | 4/2003 |
| EP | 2201932 A1 | 6/2010 |
| EP | 2736481 B1 | 7/2017 |
| WO | 2006026851 A1 | 3/2006 |
| WO | 2008/055756 A2 | 5/2008 |
| WO | 2012025269 A2 | 3/2012 |
| WO | 2016/005114 A1 | 1/2016 |
| WO | 2016005143 A1 | 1/2016 |

OTHER PUBLICATIONS

Kh. Schrader, Grundlagen and Rezepturen der Kosmetika [Cosmetic principles and formulas], 2nd Edition, Hüthig Buch Verlag, Heidelberg, 1989.
Intellectual Property Office, Search Report under Section 17(5) for United Kingdom Patent Application No. GB1804112.9 dated Oct. 24, 2018.

* cited by examiner

*Primary Examiner* — Jyothsna A Venkat
(74) *Attorney, Agent, or Firm* — Lorenz & Kopf, LLP

(57) ABSTRACT

Multi-component package unit (kit-of-parts), ready-to-use agent, and methods for reductive decolorizing of dyed keratinous fibers are provided herein. In an embodiment, a multi-component package unit includes, separately packaged, a first container (A), a second container (B), and a third container (C). The first container (A) includes a cosmetic agent (a) that includes (a1) one or multiple reducing agents chosen from the group of formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid. The second container (B) includes a cosmetic agent (b) that includes one or multiple oxidizing agents. The third container (C) includes a cosmetic agent (c) that includes (c1) one or multiple alkalizing agents. The weight ratio of the total amount of all reducing agents (a1) to the total amount of all oxidants (b1) has a value from about 50.0 to about 4.0.

5 Claims, No Drawings

SELF-HEATING AGENTS FOR REDUCTIVE DECOLORIZATION OF DYED KERATINOUS FIBERS

This application claims priority to German Patent Application DE102017204282.6, filed Mar. 15, 2017, which is incorporated herein by reference in its entirety.

TECHNICAL FIELD

The present disclosure relates to the cosmetic sector. The present disclosure relates to a multi-component package unit (kit-of-parts or kit) for reductive decolorization of dyed keratinous fibers which includes three separately packaged containers (A), (B) and (C). Container (A) contains a first cosmetic agent (a) with one or multiple reducing agents. These reducing agents are suitable for reductive decolorization of artificially dyed hair. This first agent (a) is preferably anhydrous. Container (B) contains a second cosmetic agent (b), which is preferably a hydrous formulation. This second agent (b) is exemplified by its content of one or multiple oxidants. Container (C) contains a third agent (c), which is preferably hydrous and contains one or multiple alkalizing agents. An essential feature of the present disclosure is that the reducing agent and the oxidizing agents are present in a specific quantity ratio in relation to each other in the two separate containers. The reducing agents are used in excess of 4 to 50 times in comparison with the oxidants, wherein this quantity ratio relates to the total amount of the three agents (a) plus (b) plus (c).

An additional subject of the present disclosure is a ready-to-use agent for reductive decolorization of dyed keratinous fibers which is obtained by mixing the three agents (a), (b) and (c) described above.

A third subject of the present disclosure is a method for reductive decolorization of dyed keratinous fibers, with which the multi-component package unit and/or ready-to-use decolorizing agent described above is used.

Preparations for tinting and coloring hair are an important type of cosmetic agent. They can serve to tint the natural hair color to a lesser or greater degree depending on the preferences of each and every person, achieve a completely different hair color or cover unwanted color shades, such as shades of gray, for example. Routine hair dyes are formulated either on the basis of oxidation dyes or on the basis of partially-oxidizing dyes, depending on the preferred color and/or permanency of the dye. Combinations of oxidizing dyes and partially-oxidizing dyes are frequently used to obtain special nuances.

Dyes formulated on the basis of oxidation dyes lead to brilliant and permanent color shades. However, they do require the use of strong oxidants, such as hydrogen peroxide solutions, for example. Said dyes contain oxidative dye precursors, so-called developer components and coupler components. The developer components join together or couple with one or more coupler components to form, under the influence of oxidants or atmospheric oxygen, the actual colorants per se.

Dyes formulated on the basis of partially-oxidizing dyes are often used to achieve temporary colors. Partially-oxidizing dyes are dye molecules that coat the hair itself and do not require an oxidative process to create the color. Important representatives of this dye class include triphenylmethane dyes, azo dyes, anthraquinone dyes or nitrobenzene dyes, each of which can carry cationic or anionic groups.

With all said dyeing methods, however, the color may need to be reversed, either whole or in part, for various reasons. A partial removal of the color may be the ideal solution, for example, if the color result has a darker effect on the fibers than desired. On the other hand, a complete removal of the color may be desired in some cases. It is conceivable, for example, that the hair is to be colored or tinted in a particular way for a specific occasion, and the original color is to be restored after a few days.

Technical literature also discloses decolorizing agents and methods. The oxidative decolorization of dyed hair, by employing a routine blonding agent for example, is a well-known method from the prior art. With this process, however, the fibers can also be damaged through the use of strong oxidants.

Moreover, reductive processes for decolorization have already been described. European Patent Application EP 1300136 A2 discloses, for example, a method for hair treatment, wherein the hair is colored in a first step and then reductively decolorized again in a second step. Said reductive decolorization is achieved by employing a formulation containing a diothine salt and a tenside. In WO 2008/055756 A2, the reductive decolorization of keratin fibers is achieved using a mixture formed from a reducing agent and an absorption agent.

When reductive decolorizing agents are used, the decolorization effect is achieved by reducing the dyes located on the keratin fibers and/or hair. The reduction process usually involves converting the dyes to their reduced forms and/or leuco forms. This method involves reducing the double bonds present in the dyes, thus interrupting the chromophoric system of the dyes and converting the dye into a colorless form.

Normally, strong reducing agents must be used for the reduction of dyes. These reducing agents are very reactive compounds that are often unstable in a hydrous solution and—depending on the pH value of the solution—decompose to a greater or lesser degree. For example, the reductive decolorizing agent sodium dithionite known from the prior art is sensitive to atmospheric oxygen and decomposes slowly in a hydrous solution. By increasing the pH value, this decomposition reaction can be delayed. The adjustment to a slightly alkali pH value stabilizes hydrous dithionite solutions so that the solution can be stored for several weeks to months with the absence of oxygen. However, if the reductive decolorizing agent should no longer be stored and under storage conditions with high temperatures, packaging in a solution, particularly a hydrous solution is not the method of choice.

Other reducing agents, such as formamidine sulfinic acid are unstable in hydrous solutions so that a suitable method for providing the reducing agent in a storable form is still sought. In WO 2016/005114 A1, for example, the reducing agent is incorporated into a hydrous fat-containing paste. This paste is then mixed with a hydrous formulation shortly before application and the ready-to-use decolorizing agent is produced in this manner. The reducing agent is now stable under storage for a much longer time in an anhydrous environment.

Although packaging in a paste form is a major advancement in terms of stability of the formulation, not all requirements are fulfilled with respect to the application process. In this connection, the deficient solubility of the reducing agent in the hydrous formulation, in particular is problematic. For example, formamidine sulfinic acid, which is alternatively referred to as thiourea dioxide, has especially poor water solubility with 27 g/l (measured at 20° C.).

If the user now mixes the reducing agent component (paste) with the hydrous component, they must—in order to obtain an application mixture—mix the two components together for an especially long time, stir and/or shake the mixture especially vigorously or heat up the application mixture. All of these options are uncomfortable for the user and entail the risk that only incomplete mixture is achieved despite their efforts. If this inhomogeneous application mixture is applied to the hair, this has a disadvantageous effect on the consistency of the decolorizing result.

Therefore, the present disclosure addresses the problem of providing packaging possibilities, agents and processes which enable comfortable, consistent and quick production of a ready-to-use decolorizing agent. The ready-to-use decolorizing agent produced in this manner should decolorize the keratinitic fibers as consistently and effectively as possible. Furthermore, the decolorizing agent is exemplified by high storage stability and still has a high decolorizing effect after a long storage time at high temperatures.

BRIEF SUMMARY

Multi-component package unit (kit-of-parts) for reductive decolorizing of keratin fibers, Ready-to-use agent for reductive decolorizing of dyed keratinous fibers, and methods for reductive decolorizing of dyed keratinous fibers are provided herein. In an embodiment, a multi-component package unit (kit-of-parts) for reductive decolorizing of keratin fibers includes, separately packaged, a first container (A), a second container (B), and a third container (C). The first container (A) includes a cosmetic agent (a) that includes (a1) one or multiple reducing agents chosen from the group of formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid. The second container (B) includes a cosmetic agent (b) that includes one or multiple oxidizing agents chosen from the group of hydrogen peroxide, potassium persulfate, sodium persulfate and/or ammonium persulfate. The third container (C) includes a cosmetic agent (c) that includes (c1) one or multiple alkalizing agents. The weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

In another embodiment, a ready-to-use agent for reductive decolorizing of dyed keratinous fibers includes (a1) one or multiple reducing agents chosen from the group of formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid. The agent further includes (b1) one or multiple oxidizing agents chosen from the group of hydrogen peroxide, potassium persulfate, sodium persulfate and/or ammonium persulfate. The agent further includes (c1) one or more alkalizing agents chosen from the group of ammonia, 2-aminoethan-1-ol, 2-amino-2-methylpropane-1-ol, arginine, lysine, ornithine, histidine, potassium hydroxide, sodium hydroxide, magnesium hydroxide and/or calcium hydroxide. The weight ratio of the total amount of all reducing agents (a1) contained in the agent to the total amount of all oxidants (b1) contained in the agent—relative to the total weight of the agent—has a value from about 50.0 to about 4.0.

In another embodiment, a method for reductive decolorizing of dyed keratinous fibers includes the following steps in the specified sequence. A ready-to-use decolorizing agent is produced by mixing a first agent (a), a second agent (b), and a third agent (c). Agent (a) includes (a1) one or multiple reducing agents chosen from the group of formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid. Agent (b) includes (b1) one or multiple oxidizing agents chosen from the group of hydrogen peroxide, potassium persulfate, sodium persulfate and/or ammonium persulfate. Agent (c) includes (c1) one or multiple alkalizing agents. The ready-to-use decolorizing agent is applied on dyed keratinous fibers. The decolorizing agent is allowed to take effect. The decolorizing agent is rinsed off of the keratinous fibers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it was now discovered that the problem described above can be solved in an outstanding manner if the reductive decolorizing agent is packaged in the form of a special multi-component package unit (kit-of-parts). This multi-component package unit comprises three separately packaged containers (A), (B) and (C), wherein these three containers each contain the cosmetic agents (a), (b) and (c), respectively. Agent (a) contains at least one reducing agent and is preferably anhydrous. Agent (b) is a cosmetic carrier which contains low amounts of oxidant. The third agent (c) adjusts an alkali pH value and therefore contains at least on alkalizing agent. Agent (c) is preferably packaged in a hydrous manner.

To produce the ready-for-use agent decolorizing agent, agents (a), (b) and (c) are mixed together. The reducing agent previously packaged separately comes into contact with the oxidant and the alkalizing agent during the mixing. Oxidants and reduction agents react with each other in an exothermic reaction. The reaction heat arising during this exothermic reaction heats the application mixture, and this heating leads to faster, better and more complete dissolving of the reducing agent (e.g. the formamidine sulfinic acid) in the hydrous formulation.

A central and essential feature of the present disclosure is the ratio of reducing agent to oxidant in the total amount of agent (a) plus (b) plus (c) (the mixture of (a) plus (b) plus (c) corresponds to the ready-to-apply reductive decolorizing agent). The reducing agent is used in excess of from about 4 to about 50 times in comparison with the oxidants in the total amount of agents (a) plus (b) plus (c). In this way, the reducing agents can react with the oxidant in the ready-to-use decolorizing agent. In the process, the oxidizing agent is completely consumed and the application mixture is heated. Due to the heating, the application mixture dissolves the remaining reducing agent quickly and completely and can thus be used effectively for reductive decolorizing of dyed hair. The pH value necessary for effective decolorizing is adjusted by mixing with agent (c), because agent (c) contains at least one alkalizing agent.

A first subject of the present disclosure, is a multi-component package unit (kit-of-parts) for reductive decolorizing of keratin fibers, comprising (I) a first container (A) containing a cosmetic agent (a) and (II) a second container (B) containing a cosmetic agent (b) and (III) a third container (C) containing a cosmetic agent (c), packaged separately from each other, where
agent (a) in container (A)
(a1) contains one or multiple reducing agents from the group including formamidine sulfinic acid,
sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid, and
agent (b) in container (B)
(b1) contains one or multiple oxidizing agents from the group including hydrogen peroxide, potassium persulfate, sodium persulfate and/or ammonium persulfate, and
agent (c) in container (C)
(c1) contains one or multiple alkalizing agents,
wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Keratinous fibers, keratin-containing fibers or keratin fibers are furs, wool, feathers and, in particular, human hair. Although the agents as contemplated herein are most suitable for lightening and coloring keratinous fibers and/or human hair, they can in principle be used for other purposes.

The expression "dyed keratinous fibers" means keratin fibers, which were dyed by employing conventional cosmetic dyes known to a person skilled in the art. The expression "dyed keratinous fibers" means in particular fibers that have been dyed by employing oxidative dyes and/or partially oxidizing dyes known from the prior art. In this context, explicit reference is made to the known monographies, e.g. Kh. Schrader, Grundlagen and Rezepturen der Kosmetika [Cosmetic principles and formulas], 2nd Edition, Hüthig Buch Verlag, Heidelberg, 1989, which reflect the corresponding knowledge of a person skilled in the art.

Agent (a) in Container (A)
The inventive multi-component package unit (kit-of-parts) comprises a first separately packaged container (A) with a cosmetic agent (a). Agent (a) is exemplified in that it contains at least one reducing agent from the group including formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid as an essential ingredient (a1) for the present disclosure.

Formamidine sulfinic acid is alternatively referred to as thiourea dioxide or as aminoiminomethanesulfinic acid. Formamidine sulfinic acid has the structure of formula (I), but can also be present in the form of its tautomers. Formamidine sulfinic acid has the CAS number 1758-73-2 and is commercially available from various providers, such as Sigma Aldrich.

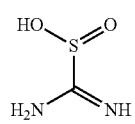

(I)

Sodium dithionite is an inorganic reducing agent and has the empirical formula $Na_2S_2O_4$ and CAS No. 7775-14-6. Zinc dithionite is an inorganic reducing agent and has the empirical formula $ZnS_2O_4$ and CAS No. 7779-86-4.

Potassium dithionite is an inorganic reducing agent and has the empirical formula $K_2S_2O_4$ and CAS No. 14293-73-3.

Hydroxymethane sulfinic acid is an inorganic reducing agent and has the empirical formula $HO-CH_2-S(O)OH$ and CAS No. 79-25-4. Hydroxymethane sulfinic acid is also referred to as formaldehyde sulfoxylic acid. As contemplated herein, both hydroxy methane sulphinic acid itself and the physiologically tolerated salts thereof, sodium salt and/or zinc salt, for example, can be used. The use of sodium formaldehyde sulfoxylate (sodium hydroxymethanesulfinate, the sodium salt of hydroxymethanesulfinic acid) and/or zinc formaldehyde sulfoxylate (zinc hydroxymethanesulfinate, the zinc salt of hydroxymethanesulfinic acid), therefore, is also inventive.

Amino methane sulfinic acid is an inorganic reducing agent and has the empirical formula $H_2N-CH_2-S(O)OH$ and CAS No. 118201-33-5. As contemplated herein, both amino methane sulphinic acid itself and the physiologically tolerated salts thereof, sodium salt and/or zinc salt, for example, can be used. The use of sodium amino methane sulfinate (sodium salt of amino methane sulphinic acid) and/or zinc amino methane sulfinate (zinc salt of amino methane sulphinic acid) is therefore contemplated herein.

As contemplated herein cysteine (2-amino-3-sulfanyl propionic acid) means D-cysteine, L-cysteine and/or a mixture of D- and L-cysteine.

Thio lactic acid (2-sulfanylpropionic acid) means D-thio-lactic acid, L-thio-lactic acid and/or a mixture of D- and L-thio lactic acid. The use of both thio lactic acid itself and also thio lactic acid in the form of a physiologically tolerable salt thereof are contemplated herein. A preferred salt of thio lactic acid is ammonium thiolactate.

Ammonium thiolactate is the ammonium salt of thio lactic acid (i.e. the ammonium salt of 2-sulfanylpropionic acid) (formula XX).

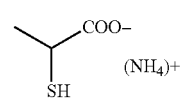

(formula XX)

Ammonium thiolactate includes, by definition, ammonium salt of D-thiolactic acid than the ammonium salt of L-thiolactic acid and mixtures thereof.

Sulfanyl acetic acid (thioglycol acid, 2-mercapto-acetic acid) is an organic reducing agent, which has the formula $HS-CH_2-COOH$ and the CAS No. 68-11-1. In the case of thioglycol acid, both the use of thioglycol acid and the use of a physiologically tolerated salt of thioglycol acid is contemplated herein. Sodium thioglycolate, potassium thioglycolate and/or ammonium thioglycolate, for example, can be used as physiologically tolerated salts of thioglycol acid. Ammonium thioglycolate is a preferred physiologically tolerated salt of thioglycol acid.

Ammonium thioglycolate is the ammonium salt of thioglycolic acid (i.e. the ammonium salt of 2-sulfanyl acetic acid) (formula XXX).

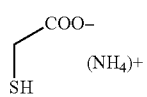

(formula XXX)

As contemplated herein, ascorbic acid means in particular (R)-5-[(S)-1,2-dihydroxyethyl]-3,4-dihydroxy-5H-furan-2-on (other alternative names: Vitamin C, L-ascorbic acid) with the CAS No. 50-81-7.

The reducing agents from the group including formamidine sulfinic acid, sodium dithionite, zinc dithionite and/or potassium dithionite has been demonstrated to be especially well-suited for use in the inventive kit. The difficulties that are associated with dissolving formamidine sulfinic acid can be avoided particularly well with the inventive kit, therefore, particular preference is given to use of formamidine sulfinic acid.

Therefore, preference is given to a multi-component package unit (kit-of-parts) for reductive decolorization of dyed keratinous fibers exemplified in that the agent (a) in the first container (A)
(a1) contains one or multiple reducing agents from the group including formamidine sulfinic acid, sodium dithionite, zinc dithionite and/or potassium dithionite, with particular preference being given to formamidine sulfinic acid.

Preference is given to a multi-component package unit (kit-of-parts) for reductive decolorizing of keratin fibers, comprising
(I) a first container (A) containing a cosmetic agent (a) and
(II) a second container (B) containing a cosmetic agent (b) and
(III) a third container (C) containing a cosmetic agent (c), packaged separately from each other, where
  agent (a) in container (A)
(a1) contains one or multiple reducing agents from the group including formamidine sulfinic acid, sodium dithionite, zinc dithionite and/or potassium dithionite, with particular preference being given to formamidine sulfinic acid, and
  agent (b) in container (B)
(b1) contains one or multiple oxidizing agents from the group including hydrogen peroxide, potassium persulfate, sodium persulfate and/or ammonium persulfate, and
  agent (c) in container (C)
(c1) contains one or multiple alkalizing agents,
  wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, preference is given to a multi-component package unit (kit-of-parts) for reductive decolorizing of keratin fibers, comprising
(I) a first container (A) containing a cosmetic agent (a) and
(II) a second container (B) containing a cosmetic agent (b) and
(III) a third container (C) containing a cosmetic agent (c), packaged separately from each other, where
  agent (a) in container (A)
(a1) contains formamidine sulfinic acid, and
  agent (b) in container (B)
(b1) contains one or multiple oxidizing agents from the group including hydrogen peroxide, potassium persulfate, sodium persulfate and/or ammonium persulfate, and
  agent (c) in container (C)
(c1) contains one or multiple alkalizing agents,
  wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

The reducing agent and/or reducing agents from group (a1) in agent (a) are preferably used in specific quantity ranges. Agent (a) preferably contains the reducing agent and/or reducing agents in a total amount of from about 5.0 to about 80.0 wt. %, preferably from about 10.0 to about 70.0 wt. %, more preferably from about 20.0 to about 60.0 wt. %, particularly from about 30.0 to about 50.0 wt. %. These specifications in percent by weight are relative to the total weight of agent (a).

Therefore, preference is given to a multi-component package unit (kit-of-parts) for reductive decolorization of dyed keratinous fibers exemplified in that the agent (a) in the first container (A) contains—relative to the total weight of agent (a)—one or multiple reducing agents (a1) in a total amount of from about 5.0 to about 80.0 wt. %, preferably from about 10.0 to about 70.0 wt. %, more preferably from about 20.0 to about 60.0 wt. %, particularly from about 30.0 to about 50.0 wt. %.

Agent (a) is an agent containing very reactive compounds and, therefore, must satisfy particularly high requirements. The undesired and premature decomposition of the reducing agents takes place to an enhanced extent in a hydrous solution, therefore it is especially preferred that agent (a) is essentially provided in an anhydrous package. In this context, the term "essential anhydrous" is understood to mean that the water content of agent (a) is about 10.0 wt. % at the most. Specific amounts of water can, for example, be introduced to the agent if a raw material in the form of a hydrate or a solution is used. The water content of agent (a), however, is preferably below about 10.0 wt. %, more preferably about 5.0 wt. %, more preferably below about 2.5%, particularly below about 0.1 wt. %. In the process, all specifications in percent by weight are relative to the total weight of agent (a).

Therefore, particular preference is given to a multi-component package unit (kit-of-parts) for reductive decolorization of dyed keratinous fibers exemplified in that the agent (a) in the first container (A) contains—relative to the total weight of agent (a)—water content below about 10.0 wt. %, preferably below about 5.0 wt. %, more preferably below about 2.5 wt. % and particularly below about 0.1 wt. %.

The essentially anhydrous agent (a) can, for example, be a powder or a paste. If agent (a) is used in the form of a powder, dust formation must be avoided and/or the powder must be dedusted. Therefore, it is particularly beneficial if agent (a) is provided in the form of a paste.

In order to obtain a pasty agent (a), for example, the reducing agent or reducing agents can be incorporated into a fat-containing carrier. In the process, the consistency of the past is co-determined by the melting point of the fat components.

Therefore, preference is given to a multi-component package unit (kit-of-parts) for reductive decolorization of dyed keratinous fibers exemplified in that the agent (a) in the first container (A)
(a2) contains one or multiple fat components (a2) from the group including $C_{12}$-$C_{30}$ fatty alcohols $C_{12}$-$C_{30}$ fatty acid triglycerides, $C_{12}$-$C_{30}$-fatty acid monoglycerides, $C_{12}$-$C_{30}$ fatty acid diglycerides, $C_{12}$-$C_{30}$ fatty acid esters, hydrocarbons and/or silicone oils.

It is particularly preferred that agent (a2) contains one or multiple fat components from the group including $C_{12}$-$C_{30}$ fatty alcohols $C_{12}$-$C_{30}$ fatty acid triglycerides, $C_{12}$-$C_{30}$-fatty acid monoglycerides, $C_{12}$-$C_{30}$ fatty acid diglycerides, $C_{12}$-$C_{30}$ fatty acid esters, hydrocarbons and/or silicone oils.

To the extent required by the present disclosure, "fatty constituents" are organic compounds with a water solubility at room temperature (22° C.) and atmospheric pressure (760 mmHg) of less than about 1 wt. %, preferably less than about 0.1 wt. %.

The definition of fatty constituents explicitly includes only uncharged (i.e. nonionic) compounds. Fatty constituents have at least one saturated or unsaturated alkyl group with at least 12 C-atoms. The molecular weight of the fatty constituents is a maximum about 5000 g/mol, preferably maximum about 2500 g/mol and even more preferably a maximum of about 1000 g/mol. The fatty constituents are neither polyoxyalkylated nor polyglycerylated compounds. In this connection, polyalkoxylated compounds are such compounds for which 2 alkylene oxide units were implemented in the production thereof. Analogously, polyglycerated compounds are such compounds for which two glycerin units were implemented in the production thereof.

Since only nonionic substances are considered fatty constituents within the context of the present disclosure, charged components, such as fatty acids and salts thereof do not fall under the group including fatty constituents.

Preferred fatty constituents are the constituents from the group including $C_{12}$-$C_{30}$ fatty alcohols $C_{12}$-$C_{30}$ fatty acid triglycerides, $C_{12}$-$C_{30}$-fatty acid monoglycerides, $C_{12}$-$C_{30}$ fatty acid diglycerides, $C_{12}$-$C_{30}$ fatty acid esters and hydrocarbons.

The $C_{12}$-$C_{30}$ fatty alcohols can be saturated, one or more unsaturated, linear or branched fatty alcohols with about 12 to about 30 C-atoms.

Examples of preferred linear, saturated $C_{12}$-$C_{30}$ fatty alcohols are dodecan-1-ol (dodecylalcohol, laurylalcohol), tetradecan-1-ol (retradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-cctadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidyl alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred typical branched fatty alcohols are 2-octyl-dodecanol, 2-hexyl-dodecanol and/or 2-butyl-dodecanol.

To the extent required by the present disclosure, a $C_{12}$-$C_{30}$ fatty acid triglyceride is the triester of the trivalent alcohol glycerine with three equivalent fatty acids. Both identically structured and different fatty acids within a triglyceride molecule can be involved in the ester formation.

To the extent required by the present disclosure, fatty acids are saturated or unsaturated, unbranched or branched, unsubstituted or substituted $C_{12}$-$C_{30}$ carboxylic acids. Unsaturated fatty acids can be unsaturated or polyunsaturated. The C—C double bond(s) of an unsaturated fatty acid can have the cis- or trans configuration.

Fatty acid diglycerides are exemplified by their particular suitability, for which at least one of the ester groups, based on glycerine, is formed with a fatty acid, which is selected from dodecan acid (laurin acid), tetradecan acid (myristine acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidic acid [(9E)-octadec-9-enic acid], erucic acid [(13Z)-docos-13-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-tetracos-15-enic acid].

The fatty acid triglycerides can also be from natural sources. The fatty acid triglycerides occurring in soy bean oil, peanut oil, sunflower oil, macadamia nut oil, drumstick tree oil, apricot kernel oil, manila oil and/or possibly hardened castor oil, and the mixtures thereof are particularly suitable for use in agent (a) as contemplated herein.

A $C_{12}$-$C_{30}$ fatty acid monoglyceride is the monoester of the trivalent alcohol glycerine with an equivalent fatty acid. Either the middle hydroxy group including the glycerine or the final hydroxy group including the glycerin can be esterified with the fatty acid.

The $C_{12}$-$C_{30}$ fatty acid triglycerides are exemplified by their particular suitability, for which at least one hydroxy group of the glycerine is esterified, wherein the fatty acids are selected from dodecan acid (laurin acid), tetradecan acid (myristine acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-Hexadec-9-enic acid], oleic acid [(9Z)-octadec-9-enic acid], elaidic acid [(9E)-octadec-9-enic acid], erucic acid [(13Z)-Docos-13-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-Icosa-5,8,11,14-trienoic acid] or nervonic acid [(15Z)-Tetracos-15-enic acid].

A $C_{12}$-$C_{30}$ fatty acid diglyceride is the diester of the trivalent alcohol glycerine with two equivalent fatty acids. Either the middle or an independent hydroxy group of the glycerine with two equivalent fatty can be esterified with two equivalent fatty acids or both final hydroxy groups of the glycerin are each esterified with one fatty acid. The glycerin can be esterified with two identically structured or two different fatty acids.

Fatty acid diglycerides are exemplified by their particular suitability, for which at least one of the ester groups, based on glycerine, is formed with a fatty acid, which is selected from dodecan acid (laurin acid), tetradecan acid (myristine acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidic acid [(9E)-octadec-9-enic acid], erucic acid [(13Z)-docos-1s3-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-tetracos-15-enic acid].

In the context of the present disclosure, a $C_{12}$-$C_{30}$ fatty acid ester is understood to mean the monoester from a fatty acid and an aliphatic monovalent alcohol, where the alcohol comprises up to about 6 carbon atoms. Suitable alcohols include, for example, ethanol, n-propanol, isopropanol, 1-butanol, isobutanol, tert-butanol, n-pentanol, iso-pentanol or n-hexanol. Ethanol and isopropanol are preferred alcohols.

Preferred $C_{12}$-$C_{30}$ fatty acid esters are the esters with which esterification of the alcohols and/or isopropanol are formed with one of the fatty acids from the group including dodecan acid (lauric acid), tetradecan acid (myristine acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidic acid [(9E)-octadec-9-enic acid], erucic acid [(13Z)-docos-13-enic acid], linoleic acid [(9Z, 12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-tetracos-15-enic acid]. Particular preference is given to isopropyl myristate as a fatty acid ester.

Hydrocarbons are exclusively compounds including hydrocarbons and hydrogen in compounds with from about 8 to about 250 carbon atoms, preferably about 150 carbon atoms. In this context, aliphatic hydrocarbons such as mineral oils, liquid paraffin oils (e.g. paraffinum liquidum or paraffinum perliquidum), isoparaffin oils, semi-solid paraffin oils, paraffin waxes, hard paraffin (paraffinum solidum), vaseline and polydecene are preferred.

In this context, liquid paraffin oils (paraffinum liquidum and paraffinum perliquidum) have proven to be particularly suitable. The most preferable hydrocarbon is paraffinum liquidum, also referred to as white oil. Paraffinum liquidum is a mixture of cleaned, saturated, aliphatic hydrocarbons, which includes mainly hydrogen chains with a C-chain distribution from about 25 to about 35 C-atoms.

The fatty constituents can be the cosmetic carrier of agent (a) and also—depending on the nature and amount of the fat which is used—have a great influence on the consistency of the agent. In this context, it has been found to be particularly preferable that agent (a) has one or multiple fatty constituents in a total amount of from about 10 to about 90 wt. %, preferably from about 20 to about 60 wt. % and particularly from about 25 to about 50 wt. %, where these quantity specifications are relative to total weight of the agent (a).

Therefore, particular preference is given to a multi-component package unit (kit-of-parts) for reductive decolorizing of dyed keratinous fibers exemplified in that agent (a) in container (A)—relative to the total weight of agent (a)—contains one or multiple fatty constituents (a2) from the group including $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils in a total amount of from about 10 to about 90 wt. %, preferably from about 20 to about 60 wt. % and particularly from about 25 to about 50 wt. %.

The use of hydrocarbons has been found to be particularly effected for reduction the formation of dust and for inerting of the reducing agent to oxygen in the air. In particular, paraffin oils and paraffin waxes have been found to be very compatible with the solid, inorganic reducing agents. For this reason, it is explicitly preferred that one or multiple hydrocarbons are used as reducing agent (a2) in a total amount of from about 15.0 to about 90.0 wt. %, preferably from about 20.0 to about 85.0 wt. %, more preferably from about 25.0 to about 80.0 wt. % and particularly from about 30.0 to about 75.0 wt. % relative to the total weight of the agent (a).

An additional preferred embodiment is a multi-component package unit (kit-of-parts) for reductive decolorizing of keratin fibers, comprising (I) a first container (A) containing a cosmetic agent (a) and
(II) a second container (B) containing a cosmetic agent (b) and
(III) a third container (C) containing a cosmetic agent (c), packaged separately from each other, where agent (a) in container (A)

(a1) contains one or multiple reducing agents from the group including formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid, and (a2) contains one or multiple fat components (a2) from the group including $C_{12}$-$C_{30}$ fatty alcohols $C_{12}$-$C_{30}$ fatty acid triglycerides, $C_{12}$-$C_{30}$-fatty acid monoglycerides, $C_{12}$-$C_{30}$ fatty acid diglycerides, $C_{12}$-$C_{30}$ fatty acid esters, hydrocarbons and/or silicone oils and agent (b) in container (B)

(b1) contains one or multiple oxidizing agents from the group including hydrogen peroxide, potassium persulfate, sodium persulfate and/or ammonium persulfate, and agent (c) in container (C)

(c1) contains one or multiple alkalizing agents, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

An additional preferred embodiment is a multi-component package unit (kit-of-parts) for reductive decolorizing of keratin fibers, comprising (I) a first container (A) containing a cosmetic agent (a) and
(II) a second container (B) containing a cosmetic agent (b) and
(III) a third container (C) containing a cosmetic agent (c), packaged separately from each other, where agent (a) in container (A)

(a1) contains one or multiple reducing agents from the group including formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid, and (a2) contains one or multiple fat components (a2) from the group including $C_{12}$-$C_{30}$ fatty alcohols $C_{12}$-$C_{30}$ fatty acid triglycerides, $C_{12}$-$C_{30}$-fatty acid monoglycerides, $C_{12}$-$C_{30}$ fatty acid diglycerides, $C_{12}$-$C_{30}$ fatty acid esters and/or hydrocarbons and agent (b) in container (B)

(b1) contains one or multiple oxidizing agents from the group including hydrogen peroxide, potassium persulfate, sodium persulfate and/or ammonium persulfate, and agent (c) in container (C)

(c1) contains one or multiple alkalizing agents, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

An additional preferred embodiment is a multi-component package unit (kit-of-parts) for reductive decolorizing of keratin fibers, comprising (I) a first container (A) containing a cosmetic agent (a) and
(II) a second container (B) containing a cosmetic agent (b) and (III) a third container (C) containing a cosmetic agent (c), packaged separately from each other, where
  agent (a) in container (A)
  (a1) formamidine sulfinic acid and
  (a2) contains one or multiple fat components (a2) from the group including $C_{12}$-$C_{30}$ fatty alcohols $C_{12}$-$C_{30}$ fatty acid triglycerides, $C_{12}$-$C_{30}$-fatty acid monoglycerides, $C_{12}$-$C_{30}$ fatty acid diglycerides, $C_{12}$-$C_{30}$ fatty acid esters and/or hydrocarbons and
  agent (b) in container (B)
  (b1) contains one or multiple oxidizing agents from the group including hydrogen peroxide, potassium persulfate, sodium persulfate and/or ammonium persulfate, and
  agent (c) in container (C)
  (c1) contains one or multiple alkalizing agents,
  wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Agent (b) in Container (B)

The second cosmetic agent (b) is contained in the second container (B) of the inventive multi-component package unit. This agent is exemplified in that it contains one or multiple oxidants from the group including hydrogen peroxide, potassium persulfate, sodium persulfate and/or ammonium persulfate.

Agent (b) is preferably hydrous or packaged in a hydrous manner. Cosmetic agent (b) can be, for example, an agent with a suitable hydrous or hydrous-alcoholic carrier. Carriers such as creams, emulsions, gels or tenside-containing, foaming solutions, such as shampoos, foaming aerosols, foam formulations or other preparations suitable for application on the hair, are used for the purpose of reductive decolorization. Agents for the reductive decolorization of keratinous fibers are preferably creams, emulsions or free-flowing gels. It is particularly preferred that agent (b) is formulated as an emulsion.

It is particularly preferred that hydrogen peroxide is used as an oxidant in agent (b). Hydrogen peroxide is especially well-suited for use in the form of a hydrous solution. If the reducing agents (a) of agent (a) come into contact with hydrogen peroxide (b1) in agent (b), the exothermic reaction which occurs is controllable and foreseeable.

Therefore, particular preference is given to a multi-component package unit (kit-of-parts) for reductive decolorization of dyed keratinous fibers exemplified in that the agent (b) in the second container (B)
(b1) contains hydrogen peroxide as an oxidant.

Therefore, preference is given to a multi-component package unit (kit-of-parts) for reductive decolorizing of dyed hair, which is packaged as separate containers.
(I) a first container (A) containing a cosmetic agent (a) and
(II) a second container (B) containing a cosmetic agent (b) and
(III) a third container (C) containing a cosmetic agent (c), packaged separately from each other, where
  agent (a) in container (A)
  (a1) contains one or multiple reducing agents from the group including formamidine sulfinic acid, sodium dithionite, zinc dithionite and potassium dithionite and
  agent (b) in container (B)
  (b1) contains hydrogen peroxide, and
  agent (c) in container (C)
  (c1) contains one or multiple alkalizing agents,
  wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Preference is also given to a multi-component package unit (kit-of-parts) for reductive decolorizing of keratin fibers, comprising
(I) a first container (A) containing a cosmetic agent (a) and
(II) a second container (B) containing a cosmetic agent (b) and
(III) a third container (C) containing a cosmetic agent (c), packaged separately from each other, where
  agent (a) in container (A)
  (a1) contains formamidine sulfinic acid
  agent (b) in container (B)
  (b1) contains hydrogen peroxide, and
  agent (c) in container (C)
  (c1) contains one or multiple alkalizing agents,
  wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Agent (b) in container (B) preferably contains—relative to the total weight of agent (b)—one or multiple oxidants (b1) in a total amount of from about 0.1 to about 10.0 wt. %, preferably from about 0.25 to about 7.5 wt. %, more preferably from about 0.5 to about 5.0 wt. % and particularly from about 0.75 to about 2.5 wt. %.

Consequently it is also preferred, in particular, that agent (b) in container (B) contains—relative to the total weight of agent (b)—from about 0.1 to about 10.0 wt. %, preferably from about 0.25 to about 7.5 wt. %, more preferably from about 0.5 to about 5.0 wt. % and particularly from about 0.75 to about 2.5 wt. %. hydrogen peroxide.

Therefore, particular preference is given to a multi-component package unit (kit-of-parts) for reductive decolorization of dyed keratinous fibers exemplified in that agent (b) in the second container (B) contains—relative to the total weight of agent (b)—one or multiple oxidants (b1) in a total amount of from about 0.1 to about 10.0 wt. %, preferably from about 0.25 to about 7.5 wt. %, more preferably from about 0.5 to about 5.0 wt. %, particularly from about 0.75 to about 2.5 wt. %.

These agents are preferably adjusted to an acidic pH value of from about 2 to about 7, preferably from about 2 to about 5 for stabilization of the oxidant in agent (b).

The pH values can, for example, be measured with a type N 61 glass electrode from the Schott company at a temperature of 22° C. To adjust the acidic pH value, agent (b) preferably contains one or multiple organic and/or inorganic acids.

To adjust the pH value, it has been found that one or multiple acids from the group including citric acid, tartaric acid, malic acid, lactic acid, acetic acid, sulphuric acid, hydrochloric acid, phosphoric acid, methane sulfonic acid, benzoic acid, malonic acid, oxalic acid, pyruvic acid, oxalocetic acid (oxobutanic acid) and/or 1-hydroxyethane-1,1-diphosphonic acid are suitable. Preferably, the acid or acids are selected from the group including citric acid, tartaric acid, malic acid, lactic acid, methanesulfonic acid, oxalic acid, malonic acid, benzoic acid, hydrochloric acid, sulphuric acid, phosphoric acid and/or 1-hydroxyethane-1,1-diphosphonic acid.

As described above, agent (b) in container (B) is preferably a hydrous cosmetic carrier formulation. The water content of this formulation is from about 30 to about 97 wt. %, preferably from about 40 to about 95 wt. %, more preferably from about 50 to about 93 wt. % and particularly from about 60 to about 91 wt. %. relative to the total weight of agent (b).

Therefore, particular preference is given to a multi-component package unit (kit-of-parts) for reductive decolorization of dyed keratinous fibers exemplified in that agent (b) contains from about 30 to about 97 wt. %, preferably from about 40 to about 95 wt. %, more preferably from about 50 to about 93 wt. % and particularly from about 60 to about 91 wt. % water relative to the total weight of agent (b).

Agent (c) in Container (C)

Different reducing agents each pass through their optimum effect in a specific pH value range. For example, ready-to-use decolorizing agents with formamidine sulfinic acid have their best effect in the alkaline range.

The ready-to-use decolorizing agent is—as described above—produced shortly before use by mixing agents (a), (b) and (c) together.

Agent (a) is preferable packaged as an anhydrous and/or pasty agent. The addition of the alkalizing agent to agent (a), can be problematic if liquid alkalizing agents are used.

Agent (b) contains one or multiple oxidants. With use of hydrogen peroxide, in particular, agent (b) should be adjusted to an acidic pH value, because hydrogen peroxide decomposes in an alkaline environment. Therefore, it is also preferred that no alkalizing agents are added to agent (b).

In order to adjust the pH value of the ready-to-use agent to an alkaline range, it has been found to be particularly advantageous to incorporate the required alkalizing agent into the third separately packaged agent (c).

The amount and strength of the alkalizing agent used in agent (c) determine the pH value of the application mixture and influences the exothermic reaction between reducing agent and oxidant.

An example of an alkalizing agent that can be use in inventive agent (c) is ammonia.

Additional alkalizing agents that can be used in inventive agent (c) can be selected, for example, from the alkanolamines. The alkanolamines usable as alkalizing agents are preferably selected from primary amines with a C2-C6-alkyl base body having at least one hydroxyl group. Preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-amino-pentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. As contemplated herein, particularly preferred alkanolamines are selected from 2-aminoethan-1-ol and/or 2-amin-2methylpropan-1-ol.

An example of alkalizing agents that can be use in inventive agent (c) is basic amino acids. An organic compound that contains at least one protonatable amino group and at least one —COOH— or —SO3H group is an amino acid in the context of the present disclosure. Preferred amino acids are amino carboxylic acids, particular α-(alpha) amine carboxylic acids and ω-amino carboxylic acids, where particular preference is given to α-amino carboxylic acids.

Basic amino acids according to the present disclosure are understood to be such amino acids which have an isoelectric point pI of greater than about 7.0.

Basic α-amino carboxylic acids contain at least one asymmetric carbon atom. In the context of the present disclosure, both possible enantiomers as a specific compound or mixtures thereof can be used as a racemate. However, it is especially advantageous to use the naturally occurring isomer form, normally in L-configuration.

The basic amino acids are preferably selected from the group that is formed of arginine, lysine, ornithine, and histidine, especially arginine and lysine. In another particularly preferred embodiment, an inventive agent (c) is exemplified in that the alkalizing agent is a basic amino acid from the group including arginine, lysine, ornithine and/or histidine.

Additional alkalizing agents that can be used in inventive agent (c) can, for example, be selected from inorganic hydoxides, such as sodium hydroxide, potassium hydroxide, magnesium hydroxide and/or calcium hydroxide.

Additional alkalizing agents that can be used in inventive agent (c) can, for example, be selected from inorganic carbonates and hydrogen carbonates, such as, for example, sodium carbonate, potassium carbonate, sodium hydrogen carbonate and/or potassium bicarbonate.

It is particularly preferable that agent (c) contains one or more alkalizing agents selected from the group including ammonia, 2-aminoethan-1-ol, 2-amino-2-methylpropane-1-ol, arginine, lysine, ornithine, histidine, potassium hydroxide, sodium hydroxide, magnesium hydroxide and/or calcium hydroxide.

Therefore, preference is given to a multi-component package unit (kit-of-parts) for reductive decolorization of dyed keratinous fibers exemplified in that the agent (c) in container (C)

(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide.

Furthermore, particular preference is given to a multi-component package unit (kit-of-parts) for reductive decolorizing of keratin fibers, which is separately packaged, comprising (I) a first container (A) containing a cosmetic agent (a) and
(II) a second container (B) containing a cosmetic agent (b) and
(III) a third container (C) containing a cosmetic agent (c) wherein agent (a) in container (A)
(a1) contains one or multiple reducing agents from the group including formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid, and agent (b) in container (B)
(b1) contains one or multiple oxidizing agents from the group including hydrogen peroxide, potassium persulfate, sodium persulfate and/or ammonium persulfate, and agent (c) in container (C)
(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, particular preference is given to a multi-component package unit (kit-of-parts) for reductive decolorizing of keratin fibers, which is separately packaged, comprising (I) a first container (A) containing a cosmetic agent (a) and
(II) a second container (B) containing a cosmetic agent (b) and
(III) a third container (C) containing a cosmetic agent (c) wherein
   agent (a) in container (A)
(a1) contains one or multiple reducing agents from the group including formamidine sulfinic acid, sodium dithionite, zinc dithionite and potassium dithionite and
   agent (b) in container (B)
(b1) contains hydrogen peroxide, and
   agent (c) in container (C)
(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, particular preference is given to a multi-component package unit (kit-of-parts) for reductive decolorizing of keratin fibers, which is separately packaged, comprising
(I) a first container (A) containing a cosmetic agent (a) and
(II) a second container (B) containing a cosmetic agent (b) and
(III) a third container (C) containing a cosmetic agent (c) wherein
   agent (a) in container (A)
(a1) contains one or multiple reducing agents from the group including formamidine sulfinic acid, sodium dithionite, zinc dithionite and potassium dithionite and
   agent (b) in container (B)
(b1) contains hydrogen peroxide, and
   agent (c) in container (C)
(c1) contains one or multiple alkalizing agents from the group including ammonia, 2-aminoethan-1-ol and/or 2-amino-2-methylpropan-1-ol,
wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, particular preference is given to a multi-component package unit (kit-of-parts) for reductive decolorizing of keratin fibers, which is separately packaged, comprising
(I) a first container (A) containing a cosmetic agent (a) and
(II) a second container (B) containing a cosmetic agent (b) and
(III) a third container (C) containing a cosmetic agent (c) wherein
   agent (a) in container (A) contains—relative to the total weight of agent (a)—
(a1) contains one or multiple reducing agents from the group including formamidine sulfinic acid, contains sodium dithionite, zinc dithionite, potassium dithionite, hydroxymethanesulfinic acid, aminomethanesulfinic acid, cysteine, thiolactic acid, sulfanylacetic acid (thioglycolic acid) and/or ascorbic acid in a total amount of from about 5.0 to about 80.0 wt. %, and
   agent (b) in container (B) contains—relative to the total weight of agent (b)—
(b1) contains one or multiple oxidizing agents from the group including hydrogen peroxide, potassium persulfate, sodium persulfate and/or ammonium persulfate in a total amount of from about 0.1 to about 5.0 wt. % and
   agent (c) in container (C)
(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, particular preference is given to a multi-component package unit (kit-of-parts) for reductive decolorizing of keratin fibers, which is separately packaged, comprising
(I) a first container (A) containing a cosmetic agent (a) and
(II) a second container (B) containing a cosmetic agent (b) and, and
(III) a third container (C) containing a cosmetic agent (c) wherein
   agent (a) in container (A) contains—relative to the total weight of agent (a)—
(a1) contains one or multiple reducing agents from the group including formamidine sulfinic acid, contains sodium dithionite, zinc dithionite, potassium dithionite, hydroxymethanesulfinic acid, aminomethanesulfinic acid, cysteine, thiolactic acid, sulfanylacetic acid (thioglycolic acid) and/or ascorbic acid in a total amount of from about 10.0 to about 70.0 wt. %, and
   agent (b) in container (B) contains—relative to the total weight of agent (b)—
(b1) one or multiple oxidizing agents from the group including hydrogen peroxide, potassium persulfate, sodium persulfate and/or ammonium persulfate in a total amount of from about 0.15 to about 2.5 wt. % and
   agent (c) in container (C)
(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, particular preference is given to a multi-component package unit (kit-of-parts) for reductive decolorizing of keratin fibers, which is separately packaged, comprising
(I) a first container (A) containing a cosmetic agent (a) and
(II) a second container (B) containing a cosmetic agent (b) and, and
(III) a third container (C) containing a cosmetic agent (c) wherein
   agent (a) in container (A) contains—relative to the total weight of agent (a)—
(a1) contains one or multiple reducing agents from the group including formamidine sulfinic acid, contains sodium dithionite, zinc dithionite, potassium dithionite, hydroxymethanesulfinic acid, aminomethanesulfinic acid, cysteine, thiolactic acid, sulfanylacetic acid (thioglycolic acid) and/or ascorbic acid in a total amount of from about 20.0 to about 60.0 wt. %, and
   agent (b) in container (B) contains—relative to the total weight of agent (b)—

(b1) contains one or multiple oxidizing agents from the group including hydrogen peroxide, potassium persulfate, sodium persulfate and/or ammonium persulfate in a total amount of from about 0.2 to about 1.0 wt. % and agent (c) in container (C)

(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Furthermore, particular preference is given to a multi-component package unit (kit-of-parts) for reductive decolorizing of keratin fibers, which is separately packaged, comprising (I) a first container (A) containing a cosmetic agent (a) and
(II) a second container (B) containing a cosmetic agent (b) and, and
(III) a third container (C) containing a cosmetic agent (c) wherein agent (a) in container (A) contains—relative to the total weight of agent (a)—

(a1) contains one or multiple reducing agents from the group including formamidine sulfinic acid, contains sodium dithionite, zinc dithionite, potassium dithionite, hydroxymethanesulfinic acid, aminomethanesulfinic acid, cysteine, thiolactic acid, sulfanylacetic acid (thioglycolic acid) and/or ascorbic acid in a total amount of from about 30.0 to about 50.0 wt. %, and agent (b) in container (B) contains—relative to the total weight of agent (b)—

(b1) one or multiple oxidizing agents from the group including hydrogen peroxide, potassium persulfate, sodium persulfate and/or ammonium persulfate in a total amount of from about 0.25 to about 0.8 wt. % and agent (c) in container (C)

(c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

It is also particularly preferred that agent (c) in container (C) is a hydrous cosmetic carrier formulation. The water content of this formulation is from about 30 to about 97 wt. %, preferably from about 40 to about 95 wt. %, more preferably from about 50 to about 93 wt. % and particularly from about 60 to about 91 wt. % relative to the total weight of agent (c).

Therefore, particular preference is given to a multi-component package unit (kit-of-parts) for reductive decolorization of dyed keratinous fibers exemplified in that agent (c) in a third container (C) contains from about 30 to about 97 wt. %, preferably from about 40 to about 95 wt. %, more preferably from about 50 to about 93 wt. % and particularly from about 60 to about 91 wt. % water relative to the total weight of agent (c).

Furthermore, particular preference is given to a multi-component package unit (kit-of-parts) for reductive decolorizing of keratin fibers, which is separately packaged, comprising (I) a first container (A) containing a cosmetic agent (a) and
(II) a second container (B) containing a cosmetic agent (b) and, and
(III) a third container (C) containing a cosmetic agent (c) wherein agent (a) in container (A) contains—relative to the total weight of agent (a)—has a water content of less than about 5.0 wt. % and (a1) contains one or multiple reducing agents from the group including formamidine sulfinic acid, sodium dithionite, zinc dithionite and/or potassium dithionite and agent (b) in container (B) contains from about 30 to about 97 wt. % water relative to the total weight of agent (b) and (b1) contains hydrogen peroxide, and agent (c) in container (C) contains from about 30 to about 97 wt. % water relative to the total weight of agent (c) and (c1) contains one or more alkalizing agents from the group including ammonia, 2-aminoethan-1-ol, 2-amino-2-methyl-propane-1-ol, arginine, lysine, ornithine, histidine, potassium hydroxide, sodium hydroxide, magnesium hydroxide and/or calcium hydroxide, and wherein the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

The alkalizing agent or alkalizing agents in agent (c) are preferably used in an amount such that the pH value of agent (c) lies in the range of from about 7.5 to about 11.5, preferably from about 8.0 to about 11.0, more preferably from about 8.0 to about 10.5, and particularly from about 8.5 to about 10.0.

Therefore, particularly preference is given to a multi-component package unit (kit-of-parts) for reductive decolorization of dyed keratinous fibers exemplified in that agent (c) in a third container (C) has a pH value in the range of from about 7.5 to about 11.5, preferably from about 8.0 to about 11.0, more preferably from about 8.0 to about 10.5 and particularly from about 8.5 to about 10.0.

Mixture of Agent (a) Plus (b) Plus (c)

To produce the ready-to-use decolorizing agent, agents (a), (b) and (c) are mixed together, whereby the total amount of agent (a) in container (A) is mixed with the total amount of agent (b) in container (B) and the total amount of agent (c) in container (C). In other words, the total amount of agents (a) plus (b) plus (c) is the ready-to-use decolorizing agent.

The sequence in which agents (a), (b) and (c) are mixed together is essentially arbitrary.

It is particularly advantageous with respect to careful control of the exothermic reaction that (anhydrous, pasty) agent (a), which contains the reducing agents, is first mixed with the alkalizing agent (c). This mixture of (a) and (c) is then mixed with the oxidizing agent preparation (b). With contact between (a)/(c) and agent (b), the exothermic reaction starts.

In the context of this embodiment, the total amount of agent (a) from container (A) is transferred to container (C) (which contains agent (c)). Then the total amount of agent (b) from container (B) is also added to container (C).

However, it can also be desired to first start the exothermic reaction between agents (a) and (b) and then dilute the mixture of (a) and (b) with the alkalizing agent (c).

In the context of this additional embodiment, the total amount of agent (a) from container (A) is transferred to container (B) (which contains agent (b)). The exothermic reaction starts in mixture (a)/(b). In order to adjust the mixture of (a) and (b) to alkaline, the total amount of agent (c) from container (C) is also added to container (B).

Since the extent of the exothermic reaction depends on the amounts of reducing agents (a1) and oxidizing agents (b1) in the ready-to-use agent (agent (a) plus (b) plus (c)), all specifications relating to the weight ratio (a1)/(b1) are also relative to the total weight of agent (a) plus (b) plus (c).

A central essential feature of the inventive kit, therefore, is that the weight ratio of the total amount of all reducing agents (a1) contained in agent (a) to the total amount of all oxidants (b1) contained in agent (b)—relative to the total weight of the agents (a) plus (b) plus (c)—has a value from about 50.0 to about 4.0.

Example 1

Container (A) contains 20 g of agent (a). Agent (a) contains (a1) 8.0 g of formamidine sulfinic acid.
Agent (a) contains 40 wt. % formamidine sulfinic acid (a1) 8.0 g/20 g=40 wt. %) relative to the total weight of agent (a).
Container (B) contains 40 g of agent (b). Agent (b) contains (b1) 0.4 g of hydrogen peroxide.
Agent (b) contains 1.0 wt. % hydrogen peroxide relative to the total weight of agent (b).
Container (C) contains 40 g of agent (c). Agent (c) contains 2.1 g of monoethanolamine.
Agent (c) is hydrous and has a pH value of 8-10.
To produce the ready-to-use decolorizing agent, 20 g of agent (a) is mixed together with 40 g of agent (b) and 40 g of agent (c) (total weight of agent (a) plus (b) plus (c)=100 g).
The total amount of agents (a)+(b)+(c) (corresponding to the ready-to-use decolorizing agent) includes:
(a1) 8.0 g of formamidine sulfinic acid (8.0 wt. % relative to agent (a) plus (b) plus (c))
(b1) 0.4 g of hydrogen peroxide (0.4 wt. % relative to agent (a) plus (b) plus (c))
The weight ratio of the total amount of all reducing agents (a1) contained in agent (a) to the total amount of all oxidants (b1) contained in agent (b)—relative to the total weight of the agents (a) plus (b) plus (c)—is 8.0 g/0.4 g=8.0 wt. %/0.4 wt. %=20.

Example 2

Container (A) contains 50 g of agent (a). Agent (a) contains (a1) 8.0 g of formamidine sulfinic acid.
Agent (a) contains 16 wt. % formamidine sulfinic acid (a1) 8.0 g/50 g=16 wt. %) relative to the total weight of agent (a).
Container (B) contains 50 g of agent (b). Agent (b) contains (b1) 0.8 g of hydrogen peroxide.
Agent (b) contains 1.6 wt. % hydrogen peroxide relative to the total weight of agent (b).
Container (C) contains 50 g of agent (c). Agent (c) contains 1.5 g of monoethanolamine.
To produce the ready-to-use decolorizing agent, 50 g of agent (a) is mixed together with 50 g of agent (b) and 50 g of agent (c) (total weight of agent (a) plus (b) plus (c)=150 g).
The total amount of agents (a)+(b)+(c) (corresponding to the ready-to-use decolorizing agent) includes:
(a1) 8.0 g of formamidine sulfinic acid (5.333 wt. % relative to agent (a) plus (b) plus (c))
(b1) 0.8 g of hydrogen peroxide (5.333 wt. % relative to agent (a) plus (b) plus (c))
The weight ratio of the total amount of all reducing agents (a1) contained in agent (a) to the total amount of all oxidants (b1) contained in agent (b)—relative to the total weight of the agents (a) plus (b) plus (c)—is 8.0 g/0.8 g=5.333 wt. %/5.333 wt. %=10.

Example 3

Container (A) contains 100 g of agent (a). Agent (a) contains (a1) 5.0 g of formamidine sulfinic acid.
Agent (a) contains 5 wt. % formamidine sulfinic acid (a1) 5.0 g/100 g=5 wt. %) relative to the total weight of agent (a).
Container (B) contains 50 g of agent (b). Agent (b) contains (b1) 1.0 g of hydrogen peroxide.
Agent (b) contains 2.0 wt. % hydrogen peroxide relative to the total weight of agent (b).
Container (C) contains 50 g of agent (c). Agent (c) contains 1.25 wt. % ammonia. To produce the ready-to-use decolorizing agent, 100 g of agent (a) is mixed together with 50 g of agent (b) and 50 g of agent (c) (total weight of agent (a) plus (b) plus (c)=200 g). The total amount of agents (a)+(b)+(c) (corresponding to the ready-to-use decolorizing agent) includes:
(a1) 5.0 g of formamidine sulfinic acid (2.5 wt. % relative to agent (a) plus (b) plus (c))
(b1) 1.0 g of hydrogen peroxide (0.5 wt. % relative to agent (a) plus (b) plus (c))
The weight ratio of the total amount of all reducing agents (a1) contained in agent (a) to the total amount of all oxidants (b1) contained in agent (b)—relative to the total weight of the agents (a) plus (b) plus (c)—is 5.0 g/1.0 g=2.5 wt. %/0.5 wt. %=5.

Consequently, reducing agent (a1) is used in excess of 4 to 50 times in comparison with the oxidants (b1) relative to the total amount of agents (a) plus (b) plus (c). This excess guarantees that there is adequate reducing agent remaining after reaction between reducing agent and oxidant in order to reductively decolorize the dyed hair. The greater the excess, the more substance there is available for reductive color removal. On the other hand, it is also more difficult to completely dissolve a large amount of reducing agent. For these reasons, the weight ratio (a1)/(b1) is preferably adjusted to specific ranges with values from about 45.0 to about 5.0, preferably from about 40.0 to about 8.0, more preferably from about 30.0 to about 12.0 and particularly from about 25.0 to about 15.0.

Example

The weight ratio of the total amount of all reducing agents (a1) contained in agent (a) to the total amount of all oxidants (b1) contained in agent (b)—relative to the total weight of the agents (a) plus (b) plus (c)—has a value from about 25.0 to about 15.0.

In the total amount of agents (a) plus (b) plus (c), from about 25 to about 15 times more reducing agent (a1) (measured in g) is used than oxidant (b1) (measured in g).

Therefore, particular preference is given to a multi-component package unit (kit of parts) for reductive decolorizing of dyed keratinous fibers exemplified in that the weight ratio of the total amount of all reducing agents (a1) contained in agent (a) to the total amount of all oxidants (b1) contained in agent (b) has a value of from about 45.0 to about 5.0, preferably from about 40.0 to about 8.0, more preferably from about 30.0 to about 12.0 and particularly from about 25.0 to about 15.0 relative to the total weight of agents (a) plus (b) plus (c).

As explained with the examples above, the weight ratio of the total amount of all reducing agents (a1) contained in agent (a) to the total amount of all oxidants (b1) contained in agent (b) relative to the total weight of the agents (a) plus (b) plus (c) is essentially determined by various factors:
(1) Amount of reducing agent (a1) used in agent (a)
(2) Amount of agent (a) in container (A)
(3) Amount of oxidant (b1) used in agent (b) and
(4) Amount of agent (b) in container (B)

Depending on the desired application conditions, a person skilled in the art can adjust these 4 factors (always subject to the requirement that the ratio condition (a1)/(b1) is fulfilled).

If a very fast and strong local heat development is desired, it is advantageous to prepare a lower amount of agent (a) in the kit, wherein agent (a) contains the reducing agents (a1) in a concentrated form—for example:
Container (A) contains 10 g of agent (a). Agent (a) contains (a1) 8.0 g of formamidine sulfinic acid.
  Agent (a) contains 80 wt. % formamidine sulfinic acid (a1) 8.0 g/10 g=80 wt. %) relative to the total weight of agent (a).
Container (B) contains 100 g of agent (b). Agent (b) contains (b1) 0.3 g of hydrogen peroxide.
  Agent (b) contains 0.3 wt. % hydrogen peroxide relative to the total weight of agent (b).
  Container (C) contains 50 g of agent (c). Agent (c) contains 2.0 g of monoethanolamine.
  To produce the ready-to-use decolorizing agent, 10 g of agent (a) is mixed together with 100 g of agent (b) and 50 g of agent (c) (total weight of agent (a) plus (b) plus (c)=160 g).
  The total amount of agents (a)+(b)+(c) (corresponding to the ready-to-use decolorizing agent) includes:
(a1) 8.0 g of formamidine sulfinic acid (5.0 wt. % relative to agent (a) plus (b) plus (c))
(b1) 0.3 g of hydrogen peroxide (0.1875 wt. % relative to agent (a) plus (b) plus (c))
The weight ratio of the total amount of all reducing agents (a1) contained in agent (a) to the total amount of all oxidants (b1) contained in agent (b)—relative to the total weight of the agents (a) plus (b) plus (c)—is 8.0 g/0.3 g=5.0 wt. %/0.1875 wt. %=26.67.

On the other hand, the exothermic reaction can be better controlled when a larger amount of agent (a) is prepared in the kit, wherein agent (a) contains reducing agents (a1) in a less concentrated form—for example:
Container (A) contains 20 g of agent (a). Agent (a) contains (a1) 4.0 g of formamidine sulfinic acid.
Agent (a) contains 20 wt. % formamidine sulfinic acid (a1) 4.0 g/20 g=20 wt. %) relative to the total weight of agent (a).
Container (B) contains 90 g of agent (b). Agent (b) contains (b1) 0.15 g of hydrogen peroxide.
  Agent (b) contains 0.16 wt. % hydrogen peroxide relative to the total weight of agent (b).
  Container (C) contains 20 g of agent (c). Agent (c) contains 2.0 g of monoethanolamine.
  To produce the ready-to-use decolorizing agent, 20 g of agent (a) is mixed together with 90 g of agent (b) and 20 g of agent (c) (total weight of agent (a) plus (b) plus (c)=130 g).
  The total amount of agents (a)+(b)+(c) (corresponding to the ready-to-use decolorizing agent) includes:
(a1) 4.0 g of formamidine sulfinic acid (3.077 wt. % relative to agent (a) plus (b) plus (c))
(b1) 0.15 g of hydrogen peroxide (0.1154 wt. % relative to agent (a) plus (b) plus (c))
The weight ratio of the total amount of all reducing agents (a1) contained in agent (a) to the total amount of all oxidants (b1) contained in agent (b)—relative to the total weight of the agents (a) plus (b) plus (c)—is 4.0 g/0.15 g=3.077 wt. %/0.115 wt. %=26.67.

Containers (A), (B) and (C) of the inventive kit-of-parts can contain agents (a), (b) and (c) in equal or different amounts.

In order to guarantee that the reducing agent dissolves as completely as possible, it is advantageous if agent (b) is provided in excess in relation to agent (a). Therefore, it is particularly advantageous that containers (A) and (B) contain agents (a) and (b) in such amounts that the quantity ratio of agent (a) to agent (b), i.e. the quantity ratio (a)/(b) has a value of from about 0.1 to about 1.0, preferably from about 0.15 to about 0.9, more preferably from about 0.3 to about 0.8 and particularly from about 0.4 to about 0.7.

Therefore, particular preference is given to a multi-component package unit (kit-of-parts) for reductive decolorization of dyed keratinous fibres exemplified in that containers (A) and (B) contain agents (a) and (b) in such amounts that the quantity ratio of agent (a) to agent (b), i.e. the quantity ratio (a)/(b) has a value of from about 0.1 to about 1.0, preferably from about 0.15 to about 0.9, more preferably from about 0.3 to about 0.8 and particularly from about 0.4 to about 0.7.

In other words, it is particularly preferred that agents (a) and (b) are contained in containers (A) and (B) of the inventive multi-component package unit in such amounts that agent (b) is provided in excess of one to ten times in comparison with agent (a).

For the same reason, it is also advantageous that agent (c) is prepared in excess in comparison with agent (a). Therefore, it is particularly advantageous that containers (A) and (C) contain agents (a) and (c) in such amounts that the quantity ratio of agent (a) to agent (c), i.e. the quantity ratio (a)/(c) has a value of from about 0.1 to about 1.0, preferably from about 0.15 to about 0.9, more preferably from about 0.3 to about 0.8 and particularly from about 0.4 to about 0.7.

Therefore, particular preference is given to a multi-component package unit (kit-of-parts) for reductive decolorization of dyed keratinous fibres exemplified in that containers (A) and (C) contain agents (a) and (c) in such amounts that the quantity ratio of agent (a) to agent (c), i.e. the quantity ratio (a)/(c) has a value of from about 0.1 to about 1.0, preferably from about 0.15 to about 0.9, more preferably from about 0.3 to about 0.8 and particularly from about 0.4 to about 0.7.

In other words, it is also particularly preferred that agents (a) and (c) are contained in containers (A) and (C) of the inventive multi-component package unit in such amounts that agent (c) is provided in excess of one to ten times in comparison with agent (a).

Example

Container (A) contains 10 g of agent (a).
Container (B) contains 100 g of agent (b).
Container (C) contains 100 g of agent (c).
The quantity ratio of agent (a) to (b), i.e. the quantity ratio (a)/(b) has a value of 10 g/100=0.1
The quantity ratio of agent (a) to (c), i.e. the quantity ratio (a)/(c) has a value of 10 g/100 g=0.1

Example

Container (A) contains 20 g of agent (a).
Container (B) contains 80 g of agent (b).

Container (C) contains 50 g of agent (c).

The quantity ratio of agent (a) to (b), i.e. the quantity ratio (a)/(b) has a value of 20 g/80 g=0.25

The quantity ratio of agent (a) to (c), i.e. the quantity ratio (a)/(c) has a value of 20 g/50 g=0.4

As contemplated herein, agent (a) is free from oxidants.

As contemplated herein, agent (b) is free from reducing agents.

As contemplated herein, agent (c) is free from oxidants and reducing agents.

3-Component System

The inventive multi-component package unit is a kit including a container (A), a container (B) and a container (C). Basically, this kit can also comprise additional containers, such as a container (D), which contains a conditioner, a shampoo or a post-treatment agent.

However, it is particularly preferred that the multi-component package unit includes exactly three containers (A), (B), and (C), i.e. agents (a), (b), and (c) are contained in the kit, but no additional separately packaged agents are present. If the addition of nurturing, cleaning or conditioning ingredients is desired in this embodiment, they can be incorporated into agent (a), agent (b), agent (c) or in two or three of agents (a), (b) and (c).

Therefore, particular preference is given to a multi-component package unit (kit-of-parts) for reductive decolorization of dyed keratinous fibers exemplified in that it includes exactly three agents (a), (b) and (c) in the three containers (A), (B) and (C).

Additional Ingredients in Agents (a), (b) and/or (c)

Agents (a), (b) and/or (c) can also contain additional ingredients and/or active ingredients. For example, the use of nonionic surfactants in agents (a), (b) and/or (c) has been found to be particularly advantageous.

The term surfactants is understood to mean amphiphilic (bifunctional) compounds having at least one hydrophobic radical and at least one hydrophilic molecule part. The hydrophobic molecule part is at least one hydrocarbon chain with from about 10 to about 30 carbon atoms. In the case of nonionic surfactants, the hydrophilic molecule part is an uncharged, highly polar structural unit.

Nonionic surfactants include, for example, at least one polyol group, a polyalkylene glycol ether group or a combination of a polyol and polyglycol ether group. Examples of such compounds include Deposit products of about 2 to about 50 mol ethylene oxide and/or about 2 to about 50 mol propylene oxide on linear and branched fatty alcohols with about 12 to about 30 carbon atoms, fatty alcohol polyglycol ether or fatty alcohol polypropylene glycol ether or mixed fatty alcohol polyethers, Deposit products of about 2 to about 50 mol ethylene oxide and/or about 2 to about 50 mol propylene oxide on linear and branched fatty acids with about 12 to about 30 carbon atoms, fatty acid polyglycol ether or fatty acid polypropylene glycol ether or mixed fatty acid polyethers, Deposit products of about 2 to about 50 mol ethylene oxide and/or about 2 to about 50 mol propylene oxide on linear and branched alkyl phenols having about 12 to about 30 carbon atoms in the alkyl group, alkyl phenolpolyglycol ethers or alkyl phenolpolypropylene ethers or mixed alkyl phenolpolyethers, with a methyl or C2-C6-alkyl radical end group-closed addition products of about 2 to about 0 moles of ethylene oxide and/or 0 to about 5 moles of propylene oxide on linear and branched fatty alcohols having about 8 to about 30 carbon atoms on fatty acids having about 8 to about 30 carbon atoms and on alkyl phenols having about 8 to about 15 carbon atoms in the alkyl group, such as the types available under the trade names Dehydol® LS, Dehydol® LT (Cognis).

C12-C30 fatty acid mono- and diesters of addition products of about 2 to about 30 moles of ethylene oxide on glycerin, addition products of about 5 to about 60 mol of ethylene oxide on hardened castor oil, Polyol fatty acid esters, such as the commercially available product Hydagen® HSP (Cognis) or Sovermol®-types (Cognis), polyalkoxylated triglycerides, polyalkoxylated fatty acid alkylesters with the formula (Tnio-1)

R1CO—(OCH2CHR2)$_w$OR3 (Tnio-1)

wherein R1CO denotes a linear branched, saturated and/or unsaturated acyl radical having about 6 to about 22 carbon atoms, R15 denotes hydrogen or methyl, R16 denotes linear or branched alkyl radicals having 1 to 4 carbon atoms and w denotes numbers from 1 to about 20, aminoxides, Hydroxy mixed ethers, as described in DE-OS 197 38 866, sorbitan fatty acid esters and addition products of ethylene oxide onto sorbitan fatty acid esters such as polysorbates, sugar fatty acid esters and addition products of ethylene oxide on sugar fatty acid esters, addition products of ethylene oxide on fatty acid alkanolamides and fatty amines, sugar-based surfactants of the type of alkyl- and alkenyl oligoglycosides or sugar-based surfactants of the type of fatty acid N-alkylpolyhydroxyalkamides.

C12-C30 fatty alcohols, C12-C30 fatty acid triglycerides, C12-C30 fatty acid monoglycerides, C12-C30 fatty acid diglycerides and C12-C30 fatty acid esters have a highly polar end group (which can also be seen in the low HLB values of the compounds of this group). In the context of the present disclosure, they are considered fatty components and, therefore, are nonionic surfactants according to the definition of the present disclosure.

Furthermore, agents (a), (b) and/or (c) can also contain one ore multiple nonionic polymers.

Polymers are macromolecules having a molecular weight of at least about 1000 g/mol, preferably at least about 2500 g/mol, more preferably at least about 5000 g/mol, which include the same, repeating organic units. Polymers are produced by polymerization of a monomer type or by polymerization of different, structurally different monomer types. If the polymer is produced by polymerization of one monomer type, it is referred to as a homopolymer. If structurally different monomer types are used in the polymerization, they are referred to as copolymers by a person skilled in the art.

The maximum molecular weight of the polymer depends on the degree of polymerization (number of polymerized monomers) and is partly determined by the polymerization method. According to the present disclosure, the maximum molecular weight of the zwitterionic polymer (d) is preferably no more than about $10^7$ g/mol, more preferably no more than about $10^6$ g/mol and even more preferably no more than about $10^5$ g/mol.

Nonionic polymers are exemplified in that they do not have any charges.

Examples of suitable nonionic polymers are vinylpyrrolidinone/vinyl acrylate copolymers, vinylpyrrolidinone, vinylpyrrolidinone/vinyl acetate copolymers, polyethylene glycols, ethylene/propylene/styrene copolymers and/or butylene/ethylene/styrene copolymers.

Moreover, the inventive agents (a) and (b) can contain additional active, auxiliary and additive ingredients, such as anionic, zwitterionic, amphoteric and/or cationic surfactants, cationic polymers such as quaternized cellulose ethers, polysiloxanes having quaternary groups, dimethyldiallylammonium chloride copolymers, acrylamide-dimethyldiallyl ammonium chloride copolymers, dimethylaminoethyl methacrylate-vinylpyrrolidinone copolymers quaternized with diethyl sulfate, vinyl pyrrolidinone-imidazolinium methochloride copolymers and quaternized polyvinyl alcohol; zwitterionic and amphoteric polymers; anionic polymers such as, for example, polyacrylic acids or crosslinked polyacrylic acids; structurants such as glucose, maleic acid and lactic acid, hair-conditioning compounds such as phospholipids, for example lecithin and kephalins; perfume oils, dimethyl isosorbide and cyclodextrins; fibre-structure-improving active ingredients, in particular mono-, di- and oligosaccharides such as, for example, glucose, galactose, fructose, fruit sugar and lactose; dyes for staining the agent; antidandruff active ingredients such as piroctone olamine, zinc omadins and climbazole; amino acids and oligopeptides; protein hydrolysates on an animal and/or vegetable basis, and in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetration substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, N2O, dimethyl ether, CO2 and air. In this context, explicit reference is made to the known monographies, e.g. Kh. Schrader, Grundlagen and Rezepturen der Kosmetika [Cosmetic principles and formulas], 2nd Edition, Hüthig Buch Verlag, Heidelberg, 1989, which reflect the corresponding knowledge of a person skilled in the art.

Decolorization of Dyed Keratinous Fibers

The inventive multi-component package unit is a system comprising agents (a), (b) and (c), which is used for decolorization of previously dyed keratinous fibers, particularly human hair. The dyed keratinous fibers are usually fibers which have been colored beforehand by employing conventional oxidative dyes and/or partially oxidative dyes known to a person skilled in the art.

The decoloration agents are suitable for removing colors produced on the keratinous fibers by employing oxidizing dyes based on developer and coupler components. If the following compounds were used as developers, the colors thus produced can easily be removed effectively and almost without subsequent post-darkening by employing the decoloration agent: p-phenylendiamine, p-toluylendiamine, N,N-bis-(β-hydroxyethyl)-p-phenylaniline, 4-N,N-bis-(β-hydroxyethyl)-amino-2-methylaniline, 2-(β-hydroxyethyl)-p-phenylendiamine, 2-(α,β-dihydroxyethyl)-p-phenylendiamine, 2-hydroxymethyl-p-phenylendiamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazole.

If the following compounds were used as couplers, the colors produced thereby can likewise be removed with very good decoloration results: m-phenylendiamine derivatives, naphthols, resorcin and resorcin derivates, pyrazolone and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-pyrazolone-5, 2,4-dichloro-3-aminophenol, 1,3-bis-(2', 4'-diaminophenoxy))-propane, 2-chloro-resorcin, 4-chloro-resorcin, 2-chloro-6-methyl-3-aminophenol, 2-amino-3-hydroxypyridine, 2-methylresorcinol, 5-methylresorcinol and 2-methyl-4-chloro-5-aminophenol. 1-naphthol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcin and 2,6-dihydroxy-3,4-dimethylpyridine.

The substrate to be decolorized can also have been dyed with partially-oxidizing dyes. Nitrophenylendiamines, nitroaminophenols, azo dyes, anthrachinones or indophenoles are particularly suitable partially-oxidizing dyes. The preferred partially-oxidizing dyes are the compounds known under the international designations and/or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzol, 2-amino-4-nitrophenol, 1,4-bis-(β-hydroxyethyl)-amino-2-nitrobenzol, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzol, 1-amino-4-(2'-hydroxyethyl)-amino-5-chlor-2-nitrobenzol, 4-amino-3-nitrophenol, 1-(2'-ureidoethyl)amino-4-nitrobenzol, 4-amino-2-nitrodiphenylamine-2'-carboxylic acid, 6-nitro-1,2,3,4-tetrahydrochinoxaline, 2-Hydroxy-1,4-naphthochinon, pikramic acid and the salts thereof, 2-amino-6-chloro-4-nitrophenol, 4-ethylamino-3-nitrobenzoic acid and 2-chloro-6-ethylamino-1-hydroxy-4-nitrobenzol.

Moreover, the substrates to be de-colorized can also be dyed with natural dyes that occur in nature, such as Henna red, Henna neutral, Henna black, chamomile blossoms sandalwood, black tea, Cascara bark, sage, logwood, madder root, catechu, ceder and alkanna root.

The decolorizing agents as contemplated herein are designed to remove said colors and therefore themselves preferably contain no dyes, more particularly no oxidative dye precursors of the developer type and/or coupler type, as well as partially-oxidizing dyes.

In another preferred embodiment, therefore, an inventive multi-component package unit (kit-of-parts) is exemplified in that the total amount of all dyes and oxidative dye precursors contained in agent (a) has a maximum value of about 0.2 wt. %, preferably about 0.1 wt. %, more preferably about 0.05 wt. % and particularly a maximum of about 0.01 wt. % relative to the total weight of the agent (a) and the total amount of all dyes and oxidative dye precursors contained in agent (b) has a maximum value of about 0.2 wt. %, preferably about 0.1 wt. %, more preferably about 0.05 wt. % and particularly a maximum of about 0.01 wt. % relative to the total weight of the agent (b) and the total amount of all dyes and oxidative dye precursors contained in agent (c) has a maximum value of about 0.2 wt. %, preferably about 0.1 wt. %, more preferably about 0.05 wt. % and particularly a maximum of about 0.01 wt. % relative to the total weight of the agent (c).

Ready-To-Use Decolorizing Agent

The ready-to-use decolorizing agent is produced by mixing the three agents (a), (b) and (c) from containers (A), (B) and (C), which preferably takes place shortly before it is applied on the keratinous fibers or hair.

A second subject of the present disclosure, therefore, is a ready-to-use agent for reductive decolorization of dyed keratinous fibers, containing (a1) one or multiple reducing agents from the group including formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid, and (b1) one or multiple oxidizing agents from the group including hydrogen peroxide, potassium persulfate, sodium persulfate and/or ammonium persulfate, and (c1) one or more alkalizing agents from the group including ammonia, 2-aminoethan-1-ol, 2-amino-2-methylpropane-1-ol, arginine, lysine, ornithine, histidine, potassium hydroxide, sodium hydroxide, magnesium hydroxide and/or calcium hydroxide, wherein the weight ratio of the total amount of all reducing agents (a1) contained in the agent to the total amount of all oxidants (b1) contained in the agent—relative to the total weight of the agent—has a value from about 50.0 to about 4.0.

Therefore, in a particularly preferred embodiment, the inventive ready-to-use agent is exemplified in that it (a1) contains one or multiple reducing agents from the group including formamidine sulfinic acid, sodium dithionite, zinc dithionite and/or potassium dithionite, with particular preference being given to formamidine sulfinic acid.

In a further particularly preferred embodiment, the inventive ready-to-use agent is exemplified in that it contains (b1) contains hydrogen peroxide as an oxidant.

In another particularly preferred embodiment, the inventive ready-to-use agent is exemplified in that it (c1) contains one or multiple alkalizing agents from the group including ammonia, 2-aminoethan-1-ol and/or 2-amino-2-methylpropan-1-ol.

In another particularly preferred embodiment, the ready-to-use agent is exemplified in that the weight ratio of the total amount of all reducing agents (a1) contained in the agent to the total amount of all oxidants (b1) contained in the agent has a value of from about 45.0 to about 5.0, preferably from about 40.0 to about 8.0, more preferably from about 30.0 to about 12.0 and particularly from about 25.0 to about 15.0 relative to the total weight of the ready-to-use agent.

A preferred embodiment is a ready-to-use agent for reductive decolorizing of keratinous fibers containing (a1) one or multiple reducing agents from the group including formamidine sulfinic acid, sodium dithionite, zinc dithionite and/or potassium dithionite, with particular preference being given to formamidine sulfinic acid, and (b1) one or multiple oxidizing agents from the group including hydrogen peroxide, potassium persulfate, sodium persulfate and/or ammonium persulfate, and (c1) one or more alkalizing agents from the group including ammonia, 2-aminoethan-1-ol, 2-amino-2-methylpropane-1-ol, arginine, lysine, ornithine, histidine, wherein the weight ratio of the total amount of all reducing agents (a1) contained in the agent to the total amount of all oxidants (b1) contained in the agent—relative to the total weight of the agent—has a value from about 50.0 to about 4.0.

A preferred embodiment is a ready-to-use agent for reductive decolorizing of keratinous fibers containing (a1) one or multiple reducing agents from the group including formamidine sulfinic acid, sodium dithionite, zinc dithionite and/or potassium dithionite, with particular preference being given to formamidine sulfinic acid, and (b1) one or multiple oxidizing agents from the group including hydrogen peroxide, potassium persulfate, sodium persulfate and/or ammonium persulfate, and (c1) one or more alkalizing agents from the group including ammonia, 2-aminoethan-1-ol, 2-amino-2-methylpropane-1-ol, arginine, lysine, ornithine, histidine, wherein the weight ratio of the total amount of all reducing agents (a1) contained in the agent to the total amount of all oxidants (b1) contained in the agent—relative to the total weight of the agent—has a value from about 50.0 to about 4.0.

A preferred embodiment is a ready-to-use agent for reductive decolorizing of keratinous fibers containing (a1) one or multiple reducing agents from the group including formamidine sulfinic acid, sodium dithionite, zinc dithionite and/or potassium dithionite, with particular preference being given to formamidine sulfinic acid, and (b1) one or multiple oxidizing agents from the group including hydrogen peroxide, potassium persulfate, sodium persulfate and/or ammonium persulfate, and (c1) one or more alkalizing agents from the group including ammonia, 2-aminoethan-1-ol, 2-amino-2-methylpropane-1-ol, arginine, lysine, ornithine, histidine, wherein the weight ratio of the total amount of all reducing agents (a1) contained in the agent to the total amount of all oxidants (b1) contained in the agent—relative to the total weight of the agent—has a value from about 40.0 to about 8.0.

A preferred embodiment is a ready-to-use agent for reductive decolorizing of keratinous fibers containing (a1) one or multiple reducing agents from the group including formamidine sulfinic acid, sodium dithionite, zinc dithionite and/or potassium dithionite, with particular preference being given to formamidine sulfinic acid, and (b1) one or multiple oxidizing agents from the group including hydrogen peroxide, potassium persulfate, sodium persulfate and/or ammonium persulfate, and (c1) one or more alkalizing agents from the group including ammonia, 2-aminoethan-1-ol, 2-amino-2-methylpropane-1-ol, arginine, lysine, ornithine, histidine, wherein the weight ratio of the total amount of all reducing agents (a1) contained in the agent to the total amount of all oxidants (b1) contained in the agent—relative to the total weight of the agent—has a value from about 30.0 to about 12.0.

A preferred embodiment is a ready-to-use agent for reductive decolorizing of keratinous fibers containing (a1) one or multiple reducing agents from the group including formamidine sulfinic acid, sodium dithionite, zinc dithionite and/or potassium dithionite, with particular preference being given to formamidine sulfinic acid, and
(b1) one or multiple oxidizing agents from the group including hydrogen peroxide, potassium persulfate, sodium persulfate and/or ammonium persulfate, and
(c1) one or more alkalizing agents from the group including ammonia, 2-aminoethan-1-ol, 2-amino-2-methylpropane-1-ol, arginine, lysine, ornithine, histidine,
wherein the weight ratio of the total amount of all reducing agents (a1) contained in the agent to the total amount of all oxidants (b1) contained in the agent—relative to the total weight of the agent—has a value from about 25.0 to about 15.0.

A preferred embodiment is a ready-to-use agent for reductive decolorizing of keratinous fibers containing
(a1) one or multiple reducing agents from the group including formamidine sulfinic acid, sodium dithionite, zinc dithionite and/or potassium dithionite, with particular preference being given to formamidine sulfinic acid, and
(b1) hydrogen peroxide, and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 50.0 to about 4.0.

A preferred embodiment is a ready-to-use agent for reductive decolorizing of keratinous fibers containing
(a1) one or multiple reducing agents from the group including formamidine sulfinic acid, sodium dithionite, zinc dithionite and/or potassium dithionite, with particular preference being given to formamidine sulfinic acid, and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the ready-to-use agent—relative to the total weight of the agent—has a value from about 50.0 to about 4.0.

A preferred embodiment is a ready-to-use agent for reductive decolorizing of keratinous fibers containing
(a1) one or multiple reducing agents from the group including formamidine sulfinic acid, sodium dithionite, zinc dithionite and/or potassium dithionite, with particular preference being given to formamidine sulfinic acid, and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 40.0 to about 8.0.

A preferred embodiment is a ready-to-use agent for reductive decolorizing of keratinous fibers containing
(a1) one or multiple reducing agents from the group including formamidine sulfinic acid, sodium dithionite, zinc dithionite and/or potassium dithionite, with particular preference being given to formamidine sulfinic acid, and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 30.0 to about 12.0.

A preferred embodiment is a ready-to-use agent for reductive decolorizing of keratinous fibers containing
(a1) one or multiple reducing agents from the group including formamidine sulfinic acid, sodium dithionite, zinc dithionite and/or potassium dithionite, with particular preference being given to formamidine sulfinic acid, and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 25.0 to about 15.0.

A preferred embodiment is a ready-to-use agent for reductive decolorizing of keratinous fibers containing
(a1) formamidine sulfinic acid and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 50.0 to about 4.0.

A preferred embodiment is a ready-to-use agent for reductive decolorizing of keratinous fibers containing
(a1) formamidine sulfinic acid and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 50.0 to about 4.0.

A preferred embodiment is a ready-to-use agent for reductive decolorizing of keratinous fibers containing
(a1) formamidine sulfinic acid and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 40.0 to about 8.0.

A preferred embodiment is a ready-to-use agent for reductive decolorizing of keratinous fibers containing
(a1) formamidine sulfinic acid and
(b1) hydrogen peroxide and
(c1) one or multiple alkalizing agents from the group including ammonia, 2-aminoethan-1-ol and/or 2-amino-2-methylpropan-1-ol.

wherein the weight ratio of the total amount of all reducing agents (a1) contained in the agent to the total amount of all oxidants (b1) contained in the agent—relative to the total weight of the agent—has a value from about 30.0 to about 12.0.

A preferred embodiment is a ready-to-use agent for reductive decolorizing of keratinous fibers containing
(a1) formamidine sulfinic acid and
(b1) hydrogen peroxide and
(c1) one or multiple alkalizing agents from the group including ammonia, 2-aminoethan-1-ol and/or 2-amino-2-methylpropan-1-ol.
wherein the weight ratio of the total amount of all reducing agents (a1) contained in the agent to the total amount of all oxidants (b1) contained in the agent—relative to the total weight of the agent—has a value from about 25.0 to about 15.0.

It is particularly preferred that the ready-to-use agent is hydrous. The pH value of the ready-to-use agent is preferably in the alkaline range.

In a further particularly preferred embodiment, a ready-to-use agent for reductive decolorization of dyed keratinous fibers is exemplified in that it contains water and has a pH value in the range of from about 7.5 to about 11.5, preferably from about 8.0 to about 11.0, more preferably from about 8.0 to about 10.5 and particularly from about 8.5 to about 10.0.

With respect to other preferred embodiments of the ready-to-use decolorizing agent, the statements made regarding the multi-component package unit as contemplated herein apply mutatis mutandis.

All other particularly preferred embodiments are such embodiments that were described for the inventive kit-of-parts.

Procedure

The inventive multi-component package units (kit-of-parts described above can be used in a method for reductive decolorization.

A third subject of the present disclosure is a method for reductive decolorization of keratinous fibers, including the following steps in the specified sequence.
(I) Production of a ready-to-use decolorizing agent by mixing a first agent (a) with a second agent (b) and a third agent (c), wherein
  agent (a) is the agent disclosed in detail in the description of the first subject of the present disclosure, and
  agent (b) is the agent disclosed in detail in the description of the first subject of the present disclosure, and
  agent (c) is the agent disclosed in detail in the description of the first subject of the present disclosure, and
(II) application of the ready-to-use decolorizing agent on dyed keratinous fibers,
(III) allowing the decolorizing agent to take effect,
(IV) rinsing the decolorizing agent off of the keratinous fibers.

In other words, a third subject of the present disclosure is a method for reductive decolorization of keratinous fibers, including the following steps in the specified sequence.
(I) Production of a ready-to-use decolorizing agent by mixing a first agent (a) with a second agent (b) and a third agent (c), wherein
  agent (a)
  (a1) contains one or multiple reducing agents from the group including formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and/or ascorbic acid, and
  agent (b)
  (b1) contains one or multiple oxidizing agents from the group including hydrogen peroxide, potassium persulfate, sodium persulfate and/or ammonium persulfate, and
  agent (c)
  contains at least one alkalizing agent,
wherein the weight ratio of all reducing agents (a1) in the ready-to-use to the total amount of all oxidants (b1)—relevant to the total weight of the ready-to-use agent—has a value of from about 50.0 to about 4.0,
(II) application of the ready-to-use decolorizing agent on dyed keratinous fibers,
(III) allowing the decolorizing agent to take effect,
(IV) rinsing the decolorizing agent off of the keratinous fibers.

In step (I) the ready-to-use decolorizing agent is produced by mixing agents (a), (b) and (c). Agents (a), (b) and (c) are the three agents of the inventive multi-component package unit. With respect to other preferred embodiments of agents (a), (b) and (c), the statements made regarding the multi-component package unit as contemplated herein apply mutatis mutandis.

In step (II), the ready-to-use agent produced by mixing of agents (a), (b) and (c) is applied to the keratinous fibers or hair. With respect to other preferred embodiments of the ready-to-use agent, the statements made regarding the multi-component package unit and the ready-to-use agent as contemplated herein apply mutatis mutandis.

Based on the exothermic reaction described above, which is initiated by mixing agents (a) and (b) (and supported by mixing with agent (c)), the ready-to-use agent heats up. This heating ensures that the reducing agent (a1) is completely dissolved, but can also be used to enhance the decolorizing result. The testing conducted in the context of the present disclosure has shown that application of the heated agent (in comparison to application of the agent at room temperature) achieves a further improvement of the decolorizing result. In order to utilize this additional benefit, it is particularly preferred that a period of about 10 seconds to about 30 minutes, preferably from about 10 seconds to about 15 minutes and particularly from about 10 seconds to about 10 minutes passes between steps (I) and (II). In other words, it is particularly preferred that a maximum period of about 30 minutes, preferably about 15 minutes, particularly about 10 minutes passes between the production of the ready-to-use agent and its application on the hair.

In a further embodiment, particular preference is given to a method exemplified in that a period of from about 10 seconds to about 30 minutes, preferably from about 10 seconds to about 15 minutes and particularly from about 10 seconds to about 10 minutes passes between steps (I) and (II).

After application of the ready-to-use decolorizing agent on dyed keratinous fibers (step II), the ready-to-use decolorizing agent is left on the keratinous to take effect. The application period can be selected according to the desired decolorizing effect. For example, the decolorizing agent can be left on the hair to take effect for a period of from about 5 to about 60 minutes, preferably from about 10 to about 55 minutes, more preferably from about 20 to about 55 minutes, particularly from about 30 to about 45 minutes In a further preferred embodiment, particular preference is given to a method exemplified in that agents (a) and (b) are mixed together in a ratio (a)/(b) of from about 0.1 to about 1.0, preferably from about 0.15 to about 0.9, more preferably from about 0.3 to about 0.8 and particularly from about 0.4 to about 0.7.

In a further preferred embodiment, particular preference is given to a method exemplified in that agents (a) and (c) are mixed together in a ratio (a)/(c) of from about 0.1 to about 1.0, preferably from about 0.15 to about 0.9, more preferably from about 0.3 to about 0.8 and particularly from about 0.4 to about 0.7.

In a further preferred embodiment, particular preference is given to a method exemplified in that mixing agents (a), (b) and (c) (i.e. the ready-to-use decolorizing agent) is hydrous and has a pH value of from about 7.5 to about 12.5, preferably from about 8.0 to about 11.5, more preferably from about 8.5 to about 10.5 and particularly from about 8.5 to about 9.5.

With respect to other preferred embodiments of the inventive method, the statements made regarding the multi-component package unit and the ready-to-use agent as contemplated herein apply mutatis mutandis.

EXAMPLES 1.1. Coloration
The following formulations were produced (all data in wt. %):
Dye cream (F1)

| Raw material | wt. % |
| --- | --- |
| Cetearyl alcohol | 8.5 |
| C12-C18 fatty alcohols | 3.0 |
| Ceteareth-20 | 0.5 |
| Ceteareth-12 | 0.5 |
| Plantacare 1200 UP (laurylglucoside, 50-53% hydrous solution) | 2.0 |
| Sodium laureth-6 carboxylate (21% i hydrous solution) | 10.0 |
| Sodium myreth sulfate (68-73% hydrous solution) | 2.8 |
| Sodium acrylate, trimethylammoniopropylacrylamide chloride copolymer (19-21% hydrous solution) | 3.8 |
| Potassium hydroxide | 0.83 |
| p-toluylendiamine, sulfate | 2.25 |
| m-aminophenol | 0.075 |
| 2-amino-3-methylphenol | 0.12 |
| Resorcin | 0.62 |
| 4-chlorresorcin | 0.26 |
| 3-amino-2-methylamino-6-methoxypyridin | 0.04 |
| 1,3-bis(2,4-diaminophenoxy)propane, tetrahydrochloride | 0.05 |
| Ammonium sulfate | 0.1 |
| Sodium sulfate | 0.4 |
| Ascorbic acid | 0.1 |
| 1-Hydroxyethane-1,1-diphosphonic acid (60% hydrous solution) | 0.2 |
| Ammonia (25% hydrous solution) | 7.2 |
| Water | Ad 100 |

Oxidant (Ox)

| Raw material | wt. % |
| --- | --- |
| Sodium benzoate | 0.04 |
| Dipicolinic acid | 0.1 |
| Di-sodium pyrophosphate | 0.1 |
| Potassium hydroxide | 0.09 |
| 1,2-Propylenglycol | 1.0 |
| 1-Hydroxyethane-1,1-diphosphonic acid (60% hydrous solution) | 0.25 |
| Paraffinum liquidum | 0.30 |
| Steartrimonium chloride | 0.39 |
| Cetearyl alcohol | 3.4 |
| Ceteareth-20 | 1.0 |
| Hydrogen peroxide (50% hydrous solution) | 12.0 |

The dye cream (F1) and the oxidant (Ox) were then mixed together in a ratio of 1:1 and applied to the hair strands (Kerling Euro natural hair, white). The weight ratio of application mixture to hair was 4:1, exposure time 30 minutes at a temperature of 32 degrees Celsius. The strands were then rinsed with water, dried and left to rest at room temperature for at least 24 hours. The strands were dyed in a dark-brown color.

1.2. Decolorization
Containers (A), (B) and (C) were filled with the following agents (all specifications in grams):
Container (A) containing 20 g of agent (a)

| | Agent (a) |
| --- | --- |
| Versagel M 1600 (1) | 3.58 g |
| Formamidine sulfinic acid | 8.00 g |
| Paraffinum liquidum | ad 20.00 g |

(1) Versagel M 2600: INCI Paraffinium liquidum (mineral oil), ethylene/propylene/styrene-copolymer, butylene/ethylene/styrene-copolymer
Container (B) containing 40 g of agent (b).

| Agent (b) | Agent (bV) Comparison | Agent (bE) as contemplated herein |
| --- | --- | --- |
| Cetearyl alcohol | 4.0 g | 4.0 g |
| PEG-40 hydrogenated Castor Oil | 0.80 g | 0.80 g |
| Sodium laureth-sulfate (C12-C14, 2 EO) | 0.54 g | 0.54 g |
| Hydrogen peroxide | — | 0.40 g |
| Dipicolinic acid | 0.032 g | 0.032 g |
| 1-hydroxy ethane-1,1 diphosphonic acid | 0.12 g | 0.12 g |
| Water | ad 40.00 g | ad 40.00 g |

Container (C) containing 40 g of agent (c).

| | Agent (c) |
| --- | --- |
| Cetearyl alcohol | 2.00 g |
| Castor oil hydrogenated, 40 EO | 0.40 g |
| Sodium laureth-sulfate (C12-C14, 2 EO) | 0.27 g |
| Monoethanolamine | 2.1 g |
| Water | ad 40.00 g |

20 g of agent (a) were mixed with 40 g of agent (c) by stirring at room temperature to produce the ready-to-use decolorizing agent. 40 g of agent (b) were added by mixing at room temperature immediately after the mixture of (a) and (c).

The temperature of the application mixture was measured and the time after which the reducing agent (formamidine sulfinic acid) completely dissolved was measured:

| | Comparison 20 g agent (a) + 40 g agent (bV) + 40 g agent (c) | Application Mixture in Accordance with present disclosure 20 g agent (a) + 40 g agent (bE) + 40 g agent (c) |
| --- | --- | --- |
| Temperature after 20 seconds of stirring | 20° C. | 33° C. |
| Time until complete dissolving of formamidine sulfinic acid | 250 seconds | 55 seconds |

Once the reducing agent (formamidine sulfinic acid) in the ready-to-use decolorizing agent (agent (a) plus (b) plus (c)) has dissolved completely, the ready-to-use decolorizing agent was applied to the dyed hair, left there fore 60 minutes at room temperature and then rinsed off. Then the hair was dried.

The coloring on the decolorized strands was visually assessed. The evaluation of the color-intensity took place based on the following scale:

0—Strands no longer have any perceptible color (white-blond, like the original color of the Kerling Euro natural hair, white)
1—Strands colored with mild color intensity
2—Strands colored with moderate color intensity
3—Strands colored with strong color intensity
4—Color of strands like immediately after the dyeing, no decolorizing effect

| | Comparison 20 g agent (a) + 40 g agent (bV) + 40 g agent (c) | Application Mixture in Accordance with present disclosure 20 g agent (a) + 40 g agent (bE) + 40 g agent (c) |
|---|---|---|
| Color of strands after appplication and washing-out of decolorizing agent | 2 | 1 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A ready-to-use agent for reductive decolorizing of dyed hair comprising:

(a1) one or more reducing agents chosen from the group of formamidine sulfinic acid, sodium dithionite, zinc dithionite, potassium dithionite, hydroxymethanesulfinic acid, aminomethanesulfinic acid, cysteine, thiolactic acid, sulphanylacetic acid (thioglycolic acid) and ascorbic acid, wherein the reducing agent is present from about 5.0 to about 80.0 wt. %, and water is present in an amount below about 10 wt. %, based on a total weight of (a1), (b1) one or more oxidizing agents chosen from the group of hydrogen peroxide, potassium persulfate, sodium persulfate and ammonium persulfate, and wherein the amount of oxidizing agent is from about 0.1 to about 10.0 wt. %, based on a total weight of (b1), (c1) one or more alkalizing agents chosen from the group of ammonia, 2-aminoethan-1-ol, 2-amino-2-methyl-propane-1-ol, arginine, lysine, ornithine, histidine, potassium hydroxide, sodium hydroxide, magnesium hydroxide and calcium hydroxide, where the pH value of (c1) is from about 7.5 to 11.5, wherein the ratio of (a1) to (b1) has a value of from about 0.1 to about 1.0; and wherein the ratio of (a1) to (c1) has a value of from about 0.1 to about 1.0.

2. The ready-to-use agent according to claim 1 comprising (a1) one or multiple reducing agents chosen from the group of formamidine sulfinic acid, sodium dithionite, zinc dithionite and potassium dithionite.

3. The ready-to-use agent according to claim 1 comprising (b1) hydrogen peroxide as the oxidizing agent.

4. The ready-to-use agent according to claim 1 wherein the reducing agent is formamidine sulfinic acid, and the oxidizing agent is hydrogen peroxide.

5. A method for reductive decolorizing of dyed hair comprising the following steps in the specified sequence:
(I) producing a ready-to-use decolorizing agent by mixing (a1), (b1), and (c1) according to claim 1,
(II) applying the ready-to-use decolorizing agent on dyed hair,
(III) allowing the decolorizing agent to take effect, and
(IV) rinsing the decolorizing agent off of the hair.

* * * * *